United States Patent [19]

Spenlehauer et al.

[11] Patent Number: 5,683,723

[45] Date of Patent: Nov. 4, 1997

[54] NANOPARTICLES BASED ON A POLYOXYETHELENE AND POLYACTIC ACID BLOCK COPOLYMER

[75] Inventors: Gilles Spenlehauer, Cachan; Didier Bazile, Saint Maur des Fosses; Michel Veillard, Sceaux; Christian Prud'Homme; Jean-Paul Michalon, both of Lyons, all of France

[73] Assignee: Rhone-Poulenc Rorer S.A., Antony Cedex, France

[21] Appl. No.: 470,729

[22] Filed: Jun. 6, 1995

Related U.S. Application Data

[63] Continuation of Ser. No. 170,229, filed as PCT/FR92/00581 Jun. 25, 1992, published as WO93/00101 Jan. 7, 1993, abandoned.

[30] Foreign Application Priority Data

Jun. 28, 1991 [FR] France .................... 91 08041

[51] Int. Cl.$^6$ .................... A61K 9/14; A61K 9/51
[52] U.S. Cl. .................... 424/501; 514/951; 528/422; 424/1.37
[58] Field of Search .................... 424/489, 497, 424/501

[56] References Cited

U.S. PATENT DOCUMENTS

| | | | |
|---|---|---|---|
| 4,826,945 | 5/1989 | Cohn et al. | 528/76 |
| 5,078,994 | 1/1992 | Nair et al. | 424/501 |
| 5,238,714 | 8/1993 | Wallace et al. | 424/497 |
| 5,410,016 | 4/1995 | Hubbell et al. | 528/354 |

*Primary Examiner*—Peter F. Kulkosky
*Attorney, Agent, or Firm*—Ross J. Oehler

[57] ABSTRACT

The invention discloses nanoparticles offering an extended time before capture by the reticulo-endothelial system. Said particles are composed of an ethylene and/or propylene polyoxide polylactic copolymer optionally mixed with a polylactic polymer.

9 Claims, 2 Drawing Sheets

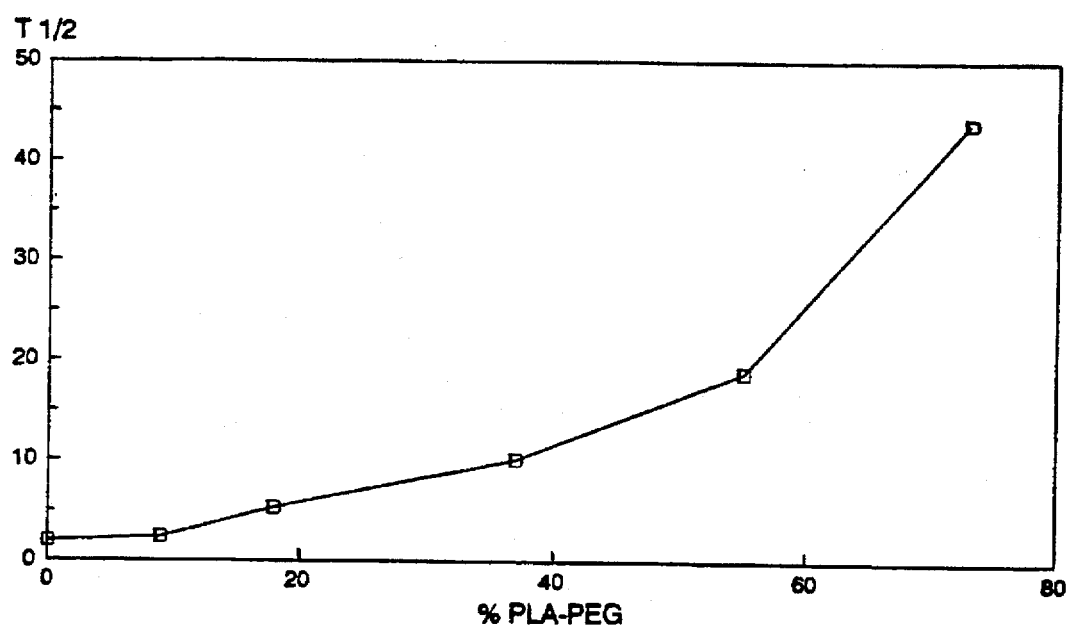

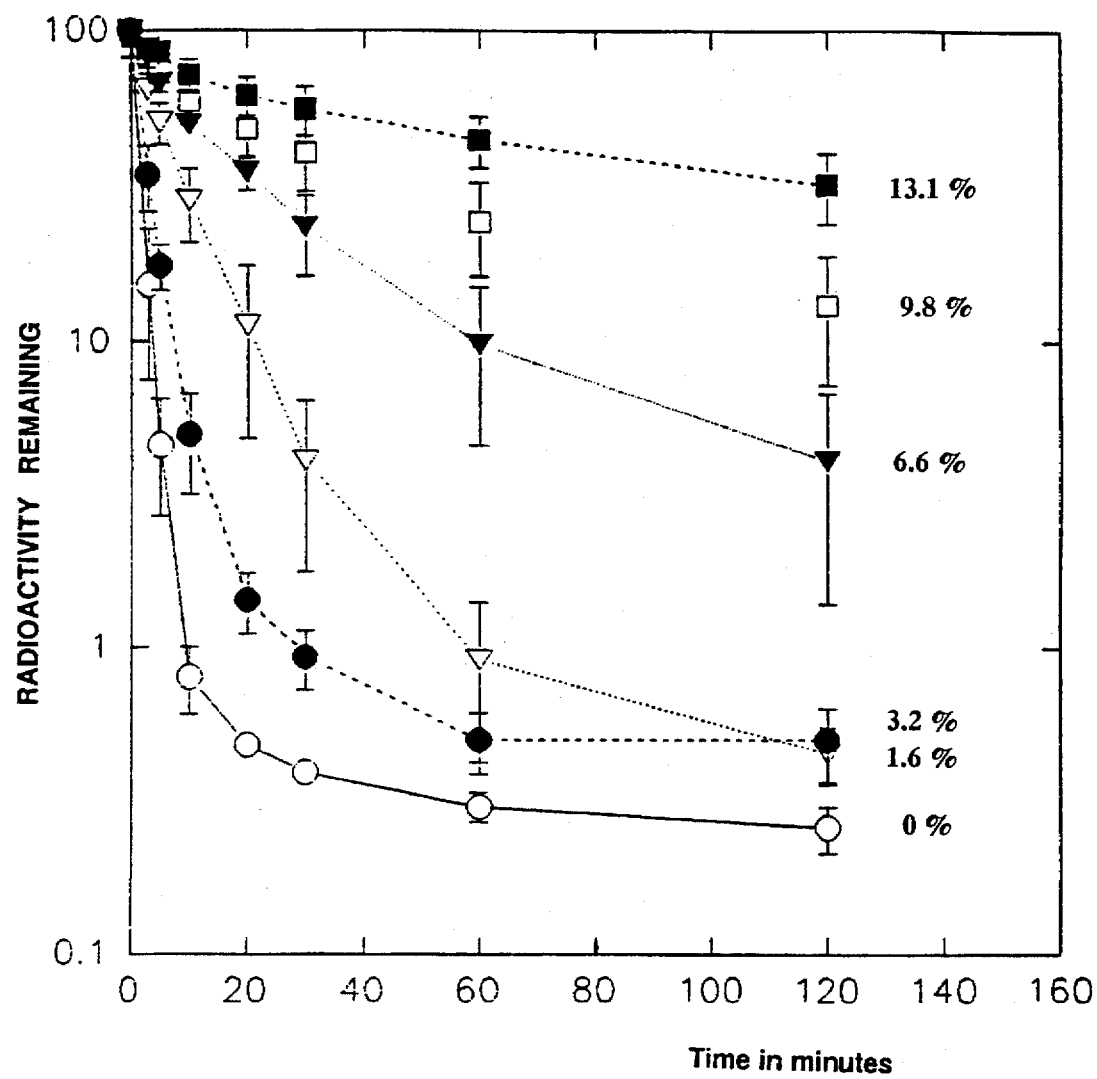

NANOPARTICLES BASED ON A POLYOXYETHELENE AND POLYACTIC ACID BLOCK COPOLYMER

This is a continuation of application Ser. No. 08/170,229 filed as PCT/FR92/00581 Jun. 25, 1992, published as WO93/00101 Jan. 7, 1993 abandoned.

The present invention relates to new, small spherical particles, often smaller than 500 nm. The new particles of the present invention, also referred to as nanoparticles, have the advantage of being able to circulate in the blood stream without there being a problem of size in the capillaries, and have the further advantage of being able to evade the reticuloendothelial system. The invention also relates to the use of the new particles according to the invention in human or animal pharmacy.

Nanoparticles which can be used for injection into the living system must be biocompatible. Thus, all polymer systems not containing biodegradable or bioresorbable polymer chains are unacceptable for such injections. It is, moreover, preferable, when such systems are used, for the degradation products to be compatible with living organisms. To date, only two types of polymers are capable of being suitable; they are lactic or glycolic polymers or lactic-glycolic mixed copolymers.

The processes for preparing nanoparticles may be divided into three types of process, the first consisting in polymerising the monomers and forming the nanoparticles simultaneously, and the other two consisting in solubilising the polymer and forming the nanoparticles independently.

The first type of process consists in performing a polymerisation of a monomer in a solution so as to obtain a micellar dispersion of the polymer in the solution. This type of process is limited to monomers which can be polymerised in solution; it necessitates removal, after the polymerisation step, of the polymerisation catalyst, the low molecular weight oligomers, the monomers and the surfactants needed for the polymerisation. The polymer obtained has a random molecular weight distribution.

The second and third types of process consist in using preformed polymers, in solubilising them in a solvent, in forming a precipitate or a dispersion from a solution of these polymers and a non-solvent, and then in evaporating off the solvent so as to recover the nanoparticles in the form of a colloidal suspension. The solvent solution is generally an organic solution of the polymer, and the non-solvent solution is often an aqueous solution.

According to the second type of process, the polymer is solubilised in a water-miscible organic solvent. When this solution is mixed with the aqueous phase, the polymer insoluble in the aqueous phase, the polymer insoluble in the aqueous phase/organic solvent mixture precipitates in the form of nanoparticles.

According to the third type of process, a water-immiscible organic solvent containing the polymer is emulsified in an aqueous phase, and the organic solvent is then evaporated off.

Formation of the precipitate or the emulsion requires the presence of a far from negligible amount of surfactant. Now, during the subsequent evaporation, it is very difficult to remove the surfactant remaining in the colloidal suspension of nanoparticles obtained; this surfactant is often undesirable in the interest of good biocompatibility. Renee the latter two techniques cannot be used for the preparation of biocompatible nanoparticles because of the presence of the colloidal protective agent.

The present invention relates to new nanoparticles which evade the reticuloendothelial system, based on polymers containing a majority of degradable units, and which optionally contain no additional surfactant. They are obtained from a copolymer consisting of a majority of polylactic units and a minority of ethylene oxide and/or propylene oxide units. This copolymer preferably corresponds, for the majority of its units, to the following formula (I):

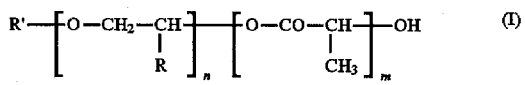

in which:
R represents, in each of the alkylene oxide units, an identical or different group chosen from hydrogen or a methyl group,
R' represents hydrogen or an alkyl group containing 1 to 4 carbon atoms, preferably a methyl group,
n is an integer between 20 and 1000,
m is an integer between 10 and 1500.

The polylactic polymeric unit of this copolymer of formula (I) preferably has a molecular weight of between 700 and 100,000; the poly(ethylene oxide) unit, for its part, preferably has a molecular weight of between 1,000 and 40,000. Still more preferably, the polylactic polymeric unit has a molecular weight of between 1,000 and 60,000, and the poly(ethylene oxide) unit has a molecular weight of between 1,000 and 6,000.

According to a final preference, the polylactic polymer is a polymer containing 50% of lactic units of D configuration (PLA$_{50}$) and the poly(alkylene oxide) is a poly(ethylene oxide).

This copolymer preferably takes the form of a diblock, i.e., according to a practical manner of implementation, the starting material is a monofunctional commercial polyethylene and/or poly(propylene oxide) of desired molecular weight, i.e. of molecular weight between 1,000 and 40,000, or alternatively containing 20 to 1,000 ethylene oxide or propylene oxide units, and preferably containing 20 to 150 ethylene oxide units or 20 to 100 propylene oxide units, onto which starting material lactide units are grafted until the desired molecular weight is obtained on the polylactic chain, in the presence of an initiator such as, in particular, tin octoate.

It may be pointed out that, to obtain polylactic blocks of molecular weight between 1,000 and 60,000, it is desirable to introduce between approximately 10 and 1,000 lactide units. It is most especially preferable to use polylactic poly(ethylene oxide) and/or poly(propylene oxide) copolymers in which the chain contains between 10 and 150 lactic units.

It is still more especially preferable to start with a commercial polyethylene glycol of molecular weight 2,100 containing 48 ethylene oxide units, which is reacted with 40 to 150 lactide units.

These new nanoparticles which evade the reticuloendothelial system can also consist of a mixture of one or more pure polylactic polymer(s) and the copolymer of formula (I).

In order to prepare the latter new nanoparticles according to the invention, it is necessary to mix the copolymer of formula (I) with an appropriate amount of a polylactic polymer. This polylactic polymer is preferably a polymer containing a 50:50 mixture of D and L isomers of lactic acid ($PLA_{50}$). It is preferable to use a mixture containing between 10 and 80% by weight of copolymer of formula (I) relative to the polylactic polymer. The final weight ratio in the polymer composition between the poly(ethylene oxide) and/ or poly(propylene oxide) unit and the polylactic units is preferably between 1 and 25% by weight. It is most especially preferable to use the composition obtained by mixing a polylactic polymer of molecular weight 60,000 and a copolymer of formula (I) in which R represents hydrogen, n is equal to 48 and m is equal to 133.

According to a first method for preparing the nanoparticles, the desired poly(ethylene oxide) and/or poly (propylene oxide) polylactic copolymer, optionally mixed with the polylactic polymer, is dissolved in a solvent or in a mixture of solvents, and the organic solution is then poured into an aqueous solution so as to cause formation of the nanoparticles by precipitation. In this process, optionally, no additional colloidal protective agent is used. Colloidal protective agent is understood to mean surface-active agents, including surfactants, which promote colloid formation.

The solvent or mixture of solvents which solubilises the copolymer is chosen from ketones such as acetone, cyclic ethers such as tetrahydrofuran and dioxanes, and nitriles such as acetonitrile. It is preferable to use acetone. The solubility of the copolymer in these solvents is preferably greater than 10 g/l.

The aqueous solution can be pure water, or a salt solution such as, e.g. a buffer solution, or alternatively a glucose solution.

The volume ratio between the aqueous solution and the solution of the copolymer is preferably between 0.5 and 10, and most especially between 1 and 10. The amount of copolymer introduced into the solvent naturally depends on its solubility but, for an improved implementation of the invention, i.e., in essence, to obtain an optimum yield of nanoparticles formed, an amount of between 10 and 50 mg/ml is preferable.

According to a second method for preparing the nanoparticles, the poly(ethylene oxide) and/or poly (propylene oxide) polylactic polymer is dissolved in an ester, preferably in ethyl acetate, and the organic solution is then poured into the aqueous solution. The nanoparticles are formed by the use of a microfluidiser.

The solvent of the copolymer is then evaporated off by heating the colloidal solution of nanoparticles above the boiling point of the solvent in the case where the removal is performed at atmospheric pressure, or to a lower temperature if the evaporation is performed under reduced pressure. After the solvent has been removed, the suspension of nanoparticles in water is filtered through a filter of pore diameter approximately 1 µm so as to remove aggregates and large particles. The yield of nanoparticles obtained generally exceeds 50%.

The formation of nanoparticles may be performed in the presence of a pharmaceutical active principle, which may be introduced either in the solvent of the copolymer or in the precipitation solvent; it should preferably be soluble in the solvent of the polymer and insoluble in water; although it is still possible to form nanoparticles if the active principle is soluble in water, the yield thereof will nevertheless be reduced.

The nanoparticles obtained contain only the copolymer of formula (I) or the mixture of polylactic polymers and copolymer of formula (I), and optionally an active principle if the precipitation is performed in the presence of an active principle. They have an average diameter of between 50 and 500 nm, and preferably an average diameter of between 50 and 250 nm.

The nanoparticles obtained are used for injection into a living organism, inasmuch as their essential advantage is that they can evade the reticuloendothelial system; thus, their main application is to be found in human or animal pharmacy, or for medical diagnosis. These products may be injected intramuscularly, subcutaneously, intro-arterially, intravenously, into organs or into cavities without risk of an anaphylactic reaction.

The invention will be described more completely by means of the examples which follow, which are not to be considered to limit the invention.

EXAMPLE 1

Preparation of Polyethylene Glycol Polylactic Copolymers 1.1) polymer $PLA^{2900}$-$PEG^{2100}$ The following are introduced into a 250 ml three-necked round-bottomed flask equipped with a paddle stirrer and a reflux condenser and under a stream of dry nitrogen, the flask being heated on a temperature-regulated oil bath:

DL-lactide . . . 144 g polyethylene . . . 79.3 g stannous octoate . . . 0.256 g toluene, distilled . . . 335 g The lactide is recrystallised on the previous day in ethyl acetate, and then washed on the day itself with ethyl ether. It is dried under vacuum. All the reactants are charged, and the mixture is then heated under gentle reflux (110°–114° C.) for 5 and a half hours. The solvent is then removed under vacuum using a rotary evaporator (40 mm Hg-100° C.).

226.3 g of concentrate are obtained.

Purification of the copolymer is performed in the following manner:

The following are charged:

concentrate . . . 215 g dichloromethane . . . 280 g

The mixture is stirred until a homogeneous solution is formed. This solution is poured slowly into 900 ml of hexane in the cold state. The polymer precipitates in the form of a paste, which is separated after settling has taken place. The polymerisation catalyst is removed in the hexane phase. After separation of the polymer, it is dried in an oven under vacuum at 40° C. 188.4 g of copolymer are obtained, the mass of which is analysed by nuclear magnetic resonance; the mass of polyethylene glycol is 2,100 and that of polylactic 2,900, representing 40 lactic units and 48 ethylene oxide units.

1.2) polymer $PLA^{9600}$-$PEG^{2100}$

Example 1.1 is repeated, introducing the following compounds:

DL-lactide ... 48.6 g polyethylene glycol ... 10 g stannous octoate ... 0.085 g toluene, distilled ... 90 g After reaction, 63.6 g of concentrate are obtained, which concentrate is purified by the following method:

40 g of concentrate are dissolved in 200 g of dichloromethane until a homogeneous solution is obtained. This solution is poured slowly into 800 ml of water maintained at between 55° and 60° C. The polymer precipitates and the dichloromethane is evaporated off, the unreacted lactide remains in aqueous solution and the polymer is centrifuged and then dried in an oven under vacuum at 40° C.

35 g of polymer are obtained, analysis of which by nuclear magnetic resonance enables the molecular weight to be determined. The latter is 9,600 for the lactic chain and 2,100 for the poly(ethylene oxide) chain, representing 133 lactic units and 48 ethylene oxide units.

1.3 polymer $PLA^{40000}$ 180 g of xylene distilled before use, and 0.180 g of tin octoate are introduced into a one-liter reactor heated on an oil bath and equipped with an anchor-shaped stirrer and a reflux condenser and maintained under nitrogen, the mixture is heated, and 120 g of DL-lactide S of the company Boehringer, recrystallised beforehand in ethyl acetate and washed with sulphuric ether, are then introduced.

The mixture is allowed to react for 5 hours at 140° C. and, at the end of the reaction, it is cooled rapidly and a portion of the xylene is then removed under vacuum. The polymer is dissolved in dichloromethane and precipitated with methanol. It is dried in a vacuum oven at 65° C.

EXAMPLE 2

Preparation of Nanoparticles from these Polymers by the First Method of Preparation 50 mg of a mixture, according to the following table, of copolymer prepared in 1.1, polylactic polymer according to 1.3 and a carbon-14-labelled polylactic polymer of molecular weight 18,000 are used, this being dissolved in 5 ml of acetone. A comparative experiment is performed using nanoparticles prepared according to the prior art, from the same polylactic polymer but in the presence of a colloidal protective agent, namely Pluronic F68 or Poloxamer 188. The nanoparticles are prepared by precipitation, pouring this volume slowly into 5 ml of 0.13 molar phosphate buffer (pH 7.4). The colloidal suspension obtained is evaporated for 30 minutes in a rotary evaporator at room temperature and at a pressure of 3 mm Hg. The suspension is then filtered through a 1.2 µm filter in order to remove large particles and aggregates.

400 µl of the suspension are injected into each rat, and the rats are divided into groups of five, one for each concentration of poly(ethylene oxide). The kinetics of uptake of the particles by the reticuloendothelial system is represented by plotting the radioactivity remaining in the plasma, as a % of the radioactivity present in the plasma at the end of perfusion, as a function of time. The half-life of the particles as a function of the amount of polyethylene glycol introduced is shown in the table below and in FIG. 1. The graph depicting radioactivity remaining in the plasma is appended as FIG. 2.

| % PEG | 0 | 0 | 1.6 | 3.2 | 6.6 | 9.8 | 13.1 |
|---|---|---|---|---|---|---|---|
| $PLA^{9600}PEG^{2100}$ | 0 | 0 | 9 | 18 | 37 | 55 | 73 |
| $PLA^{40\,000}$ | 70 | 0 | 61 | 55 | 36 | 18 | 0 |
| $^{14}C\,PLA^{18\,000}$ | 30 | 100 | 30 | 27 | 27 | 27 | 27 |
| surfactant F68 50 g/l | YES | NO | NO | NO | NO | NO | NO |
| $T_{1/2}$ in min | 1.9 | 1.8 | 2.3 | 5.2 | 10.0 | 18.7 | 43 |

Preparation of Nanoparticles from these Polymers by the Second Method of Preparation Without a Surfactant 100 mg of $PLA_{50}^{9600}PEG^{2100}$ and 10 mg of $^{14}C$-labelled poly(DL-lactic acid) of molecular weight 18,000 are used, these being dissolved in 1 ml of ethyl acetate. This solution is then dispersed using an Ultraturrax in 10 ml of water. A coarse emulsion is obtained. It is then recycled for 2 minutes using a MICROFLUIDICS type high pressure homogeniser. The ethyl acetate is cleared from the emulsion using a rotary evaporator at a pressure of 50.5 cm of mercury at 20° C. The pseudolatex obtained consists of nanoparticles of average diameter 145±60 nm. The half-life of these nanoparticles in the blood is 1 hour.

With a Surfactant

The procedure is the same as in the example above, dissolving 50 mg of $PLA^{9600}PEG^{2100}$, 50 mg of $PLA_{DL}^{52000}$ and 10 mg of $^{14}C$-labelled $PLA_{DL}^{18000}$, which are dissolved in 1 ml of ethyl acetate. The aqueous phase is a sodium cholate solution at a concentration of 10 g.l$^{-1}$ in water. Diameter of the nanoparticles: 105±45 nm. Half-life: 0.5 hour.

We claim:

1. Nanoparticles which evade the reticuloendothelial system, characterised in that they consist of a poly(ethylene oxide) and/or poly(propylene oxide) polylactic copolymer of units of formula:

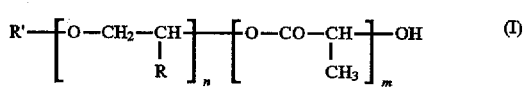

in which:

R represents, in each of the alkylene oxide units, an identical or different group chosen from hydrogen or a methyl group, R' represents hydrogen or an alkyl group containing 1 to 4 carbon atoms, n is an integer between 20 and 1000, m is an integer between 10 and 1500.

2. Nanoparticles which evade the reticuloendothelial system, characterised in that they consist of a mixture of:

a poly(ethylene oxide) and/or poly(propylene oxide) polylactic copolymer of units of formula (I)

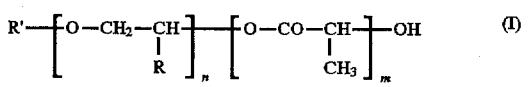

wherein R represents, in each of the alkylene oxide units, an identical or different group chosen from hydrogen or a methyl group; R' represents hydrogen or an alkyl group containing 1 to 4 carbon atoms; n is an integer between 20 and 1000;

and m is an integer between 10 and 1500;

and poly(lactic acid) polymer.

3. Nanoparticles according to claim 2, characterised in that they consist of a mixture of polymers according to claim 2 and a pharmaceutical active principle.

4. Nanoparticles according to claim 1, characterised in that, in the formula (I)

R represents hydrogen,

R' represents a methyl group, n is between 20 and 150, m is between 10 and 150.

5. Nanoparticles according to claim 1, characterised in that they have an average size of between 50 and 500 nm.

6. Nanoparticles according to claim 5, characterised in that they have an average size of between 50 and 250 nm.

7. A method for administering a pharmaceutical active principle to a patient comprising administering a therapeutically effective amount of a pharmaceutical composition comprising said principle and the nanoparticles of claim 1 to a patient.

8. The method according to claim 7, wherein said administration is injection intramuscularly, subcutaneously, intro-arterially, intravenously, into organs or into cavities.

9. A pharmaceutical carrier comprising nanoparticles of poly(ethylene oxide) and/or poly(propylene oxide) polylactic copolymer containing a majority of units of Formula I:

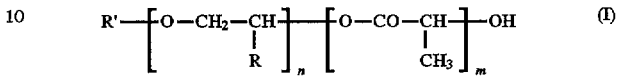

wherein R is, in each alkylene oxide units, and identical or different group chosen from hydrogen or a methyl group, R' is hydrogen or an alkyl containing 1 to 2 carbon atoms, n is an integer between 20 and 1000, m is an integer between 20 and 1500.

* * * * *

UNITED STATES PATENT AND TRADEMARK OFFICE
CERTIFICATE OF CORRECTION

PATENT NO. : 5,683,723
DATED : November 4, 1997
INVENTOR(S) : Gilles Splenlehauer, et al It is certified that error appears in the above-identified patent and that said Letters Patent is hereby corrected as shown below:

On the title page: Item [54] and Column 1, line 1-2,
*should read:*

NANOPARTICLES BASED ON A POLYOXYETHYLENE AND POLYACTIC ACID BLOCK COPOLYMER

Signed and Sealed this

Third Day of February, 1998

Attest:

BRUCE LEHMAN

Attesting Officer

Commissioner of Patents and Trademarks